United States Patent [19]
Bell

[11] Patent Number: 5,879,330
[45] Date of Patent: Mar. 9, 1999

[54] NEEDLE REMOVAL AND CONTAINMENT DEVICE AND METHOD OF USING SAME

[75] Inventor: Craig J. Bell, E. Swanzey, N.H.

[73] Assignee: MedCare Medical Group, Inc., E. Swanzey, N.H.

[21] Appl. No.: 910,928

[22] Filed: Aug. 8, 1997

[51] Int. Cl.⁶ ........................................... A61M 5/32
[52] U.S. Cl. .................. 604/93; 604/49; 604/175; 604/187
[58] Field of Search .................. 604/93, 175, 187, 604/192, 198, 263, 49, 51, 52–54, 905, 164, 165, 162, 171, 177

[56] References Cited

U.S. PATENT DOCUMENTS

| | | |
|---|---|---|
| 4,581,020 | 4/1986 | Mittleman ............................ 604/175 |
| 5,135,502 | 8/1992 | Koenig, Jr. et al. ............... 604/175 X |
| 5,248,301 | 9/1993 | Koenig, Jr. et al. ................. 604/164 |
| 5,460,612 | 10/1995 | Madore . |
| 5,571,092 | 11/1996 | Thompson . |

*Primary Examiner*—John D. Yasko
*Attorney, Agent, or Firm*—Davis and Bujold

[57] ABSTRACT

A needle retraction device for removing a needle from a patient. The needle retraction device comprising a housing having an exterior wall which defines an interior compartment. A slidable member, having a pair of spaced apart movable legs separated from one another by an elongate slot, is located within the interior compartment. The pair of spaced apart movable legs are also spaced from a remainder of the slidable member by a cavity or area which is sized to receive needle therein. The slidable member is movable from a first position, in which the pair of spaced apart movable legs are located outside of the interior compartment of the needle retraction device for receiving a needle, and a second retracted position, in which the pair of spaced apart movable legs along with a supported needle, are completely retracted inside the interior compartment of the housing to prevent an inadvertent needle stick.

21 Claims, 5 Drawing Sheets

NEEDLE REMOVAL AND CONTAINMENT DEVICE AND METHOD OF USING SAME

FIELD OF THE INVENTION

The present device relates to a new medical device that allows for the safe removal and containment of a needle, such as a Huber angled needle, from a vascular access port implanted subcutaneously in the chest or other area of a patient.

BACKGROUND OF THE INVENTION

The risk of cross-contamination and infection from needle sticks are well documented in the associated literature. These include the contraction of life threatening HIV virus, several strains of hepatitis and other blood and body fluid borne diseases.

Surgically implanted vascular access ports have been used by the medical community for many years. They are a means of allowing for the easy removal of blood for laboratory testing along with providing for the repeated infusion of medication with as little discomfort to the patient as possible. These ports are placed in the chest of the patient, with a catheter extending into a blood vessel.

The port is typically constructed of biocompatible metal with a thick elastomeric membrane septum that is positioned under the surface of the skin, but accessible to needle penetration. The septum makes it possible for a needle to penetrate the port to an inner septum chamber for the infusion of a drug through the needle into the port, followed by the needle's removal without leakage from the port. The purpose of the port is to allow for easy drug delivery without excess needle sticks to the patient, however, the thickness of the port's septum increases the potential of an inadvertent needle stick to the patient or care giver during the withdrawal of the needle from the port.

The type of needle used with the vascular ports are termed Huber angled needles. These needles are unique in that they contain a ninety degree bend halfway along the needle shaft and include handling/ securing wings located immediately adjacent the bend. The bend in the needle shaft allows the handling/securing wings to be secured to the skin of the patient with tape while the port is in use. These needles are also noncoring, which means that they are able to penetrate cleanly into the vascular port, much like a knife, but upon removal from the port, the port's septum closes completely. This is a very important feature with regard to leakage from the septum and also allows the septum to be accessed well over 1,000 times without damage to the septum.

To remove the needle, the care giver typically places his/her first and middle fingers on the port to support it. The fingers must be positioned on each side of the needle shaft to properly support the needle. Downward pressure must be supplied by the fingers during the needle's removal to stabilize the port. Care must be given, because excess drag from the needle's removal can cause the implanted catheter to disconnect from the port or pull the catheter out of the vessel. The other hand is used to remove the needle by grasping its handling/securing wings and using considerable upward force to remove the needle from the patient. The care giver, when removing the needle, may inadvertently counter this force by thrusting the needle back in the direction of the port at the hand stabilizing the port, which can lead to a needle stick to either the patient or the care giver.

The prior art discloses several attempts at addressing the needle stick problem. However, none of the proposed solutions are user friendly or low in cost. The Madore device, U.S. Pat. No. 5,460,612, discloses a device with two convex shaped prongs arranged in a "V" shape that are attached to a handle. With this device, the needle must be carried to a sharps disposal device with the potential for needle sticks occurring during the needle's placement in the device. In addition, the Madore device is preferably made of stainless steel, which would necessitate its resterilization between use, making the device labor intensive and expensive.

The Thompson device, U.S. Pat. No. 5,571,092, discloses a cylindrical shaped hollow bodied device that is open with flaps, at one end, and contains a slot in the other, where the tips of a hemostat are placed through the slot to grasp and remove the needle. Upon grasping the needle with the hemostat tips, downward pressure is placed on the top of the cylinder, the needle is forced upward into the hollow body with the flaps preventing the needle from leaving the container. The Thompson device is awkward to use, the hemostat is difficult to manipulate through the slot in the top of the container and the device is relatively expensive.

The Doyle Extractor by Safetech International, Inc. (patent pending), is a device that utilizes a disposable reverse hemostat type design, with the tips apart when the handles are together. The tips have slots in them to accommodate the needle. This device does not address the problem of needle containment once the needle is removed or the possibility of inadvertent needle sticks. Also, the potential for blood aerosol occurring is increased.

Although the prior art has attempted to accommodate all potential problems that can occur with the use of the Huber needles with vascular ports, improvements are still necessary. As the number of blood-borne diseases increases, the safety of all concerned increases. A device that is both cost effective and safe to both the patient and care giver is needed in the health-care industry of today.

SUMMARY OF THE INVENTION

Wherefore, it is an object of the present invention to overcome the aforementioned problems and drawbacks associated with the prior art designs.

The present invention generally relates to a medical device and method that allows for the safe removal and containment of a needle from a vascular access port implanted subcutaneously in the chest of a patient.

The retraction of the pair of movable legs and the angled needle is advantageous in that it prevents inadvertent needle sticks to the patient and care giver.

In another embodiment of the invention, the device contemplates a needle removing device comprising a housing having an exterior wall which defines an interior compartment and an inner slidable member having an engagement means sized to receive an angled needle. The inner slidable member is movable from a first position in which the engagement means receives the angled needle to a second retracted position in which the engagement means, along with the angled needle, are retracted inside the compartment of the housing.

In another embodiment of the invention, the angled needle removing device contemplates a method of removing an angled needle from a patient comprising the steps providing a housing with an exterior wall which defines an interior compartment, at least partially accommodating an inner slidable member within the interior compartment of the housing. The inner slidable member having a pair of inner member legs separated from one another by an elongate slot, the pair of inner member legs being spaced from a remainder. The inner slidable member having an inner member opening which is sized to receive an angled needle within the inner member opening. The pair of inner member legs facilitating accommodation of an angled needle within the opening of the inner slidable member. The inner slidable member is capable of moving from a first position in which the pair of inner member legs are located outside the compartment of the needle retraction device. The next step in the method is the receiving of the angled needle with a pair of inner member legs, followed by the moving of the pair of inner member legs along with the supported angled needle to a second retracted position in which both the inner slidable member and the supported angled needle are completely retracted inside the compartment of the housing. This is accomplished to prevent any inadvertent needle sticks to the patient or care giver.

In another embodiment of the invention, what is contemplated is a method of removing an angled needle from a patient comprising providing a housing with an exterior wall which defines an interior compartment. At least partially accommodating an inner slidable member within the interior compartment of the housing, it having an engagement means which is sized to receive an angled needle. Next, the inner slidable member is moved to a first position. The angled needle is received into the retraction device followed by moving the inner slide, along with the engaged angled needle, to a second retracted position. Both the inner slidable member and the angled needle are then retracted inside the compartment of the housing.

In a preferred embodiment, the device includes a locking mechanism. This mechanism is used to lock the inner slidable member into the second position.

In another preferred embodiment, the exterior housing of the device is provided with a device opening and a pair of device legs which are spaced apart from one another by an elongate slot. The inner member legs are located adjacent to the pair of device legs.

In another preferred embodiment, the housing of the device is provided with at least one elongate slot and an inner slide member is provided with at least one guide tab. The guide tab(s) is movable along the elongate slot(s) from the first position to the second position.

In a further preferred embodiment, the locking mechanism comprises at least one locking tab provided in at least one slot. The slot(s) is used to engage and permanently retain the guide tab(s).

In another embodiment, there is at least one pair of inner member legs. The pair of fixed legs is provided with a V-shaped opening to facilitate receiving the angled needle.

In another embodiment, the device further comprises the angled needle being connected to an extension tube for supplying a desired fluid to be dispensed to a patient. The angled needle further includes a pair of wings for facilitating use and securing the angled needle to the patient to keep the needle in place.

In a further preferred embodiment, the elongate slot of the pair of movable legs is wide enough to allow the angled needle to pass through, but is narrower than the extension tube. This facilitates retraction of the angled needle away from the patient inside the compartment of the housing.

It is not intended that the device or method be limited in any way to the types of materials used in the construction of the angled needle removing device, nor to its shape, size or number of parts. It is contemplated that a needle be angled in the range of 0°–180° and that more than one needle per device can be accommodated at any one time.

DESCRIPTION OF THE FIGURES

The invention will now be described, by way of example, with reference to the accompanying drawings in which.

DETAILED DESCRIPTION OF THE INVENTION

Briefly described, the present device relates to the safe removal and containment of a needle, such as a Huber angled needle or Huber needle/syringe assembly. The device is an improvement over the prior art in that it is cost effective, easy to manipulate, and safe to use for both the patient and the care giver.

The following description is of a preferred embodiment and is in no way meant to limit the scope of the device in its size or shape, in its ability to be either manual or automatic operated, nor limited in the materials used in its construction or in the orientation of the components.

Figure 1:
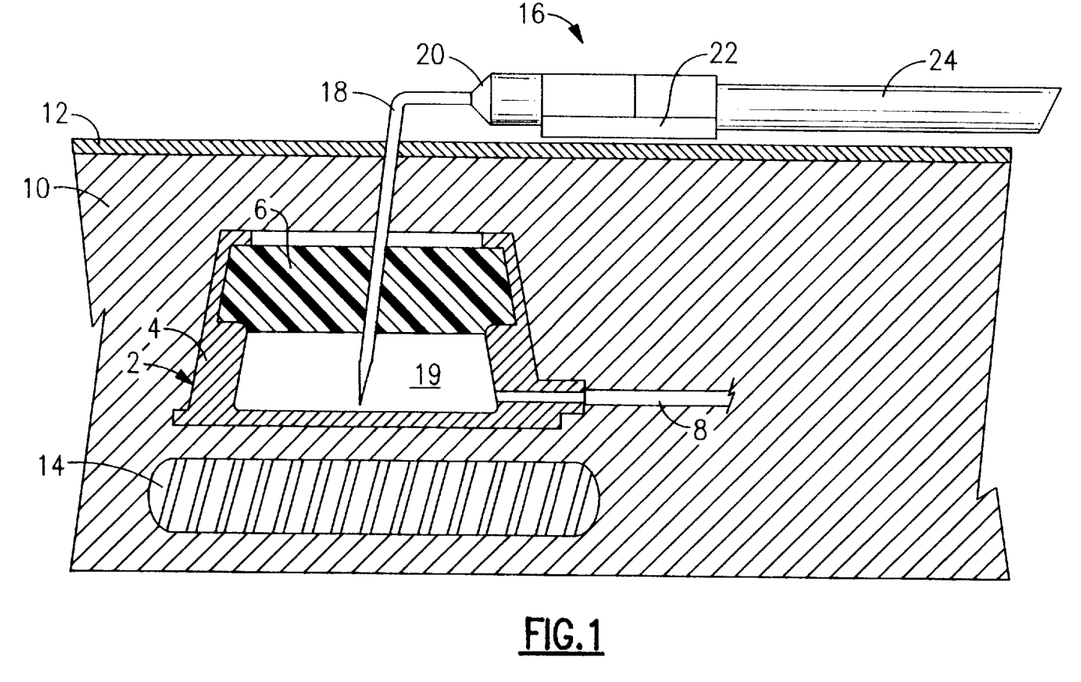
FIG. 1 illustrates a diagrammatic cross sectional view of a conventional Huber needle communicating with an implanted vascular port.

Referring first to FIG. 1, this Figure illustrates what is known in the prior art concerning use of Huber angled needle. FIG. 1 shows a diagrammatic cross sectional view of an implanted vascular port 2, constructed of a biocompatible metal housing 4 supporting an elastomeric septum 6, and coupled to a connecting catheter 8. The implanted vascular port 2 is shown positioned within the subcutaneous muscle 10, under the surface of the skin 12, and on top of a bone 14.

Figure 5:
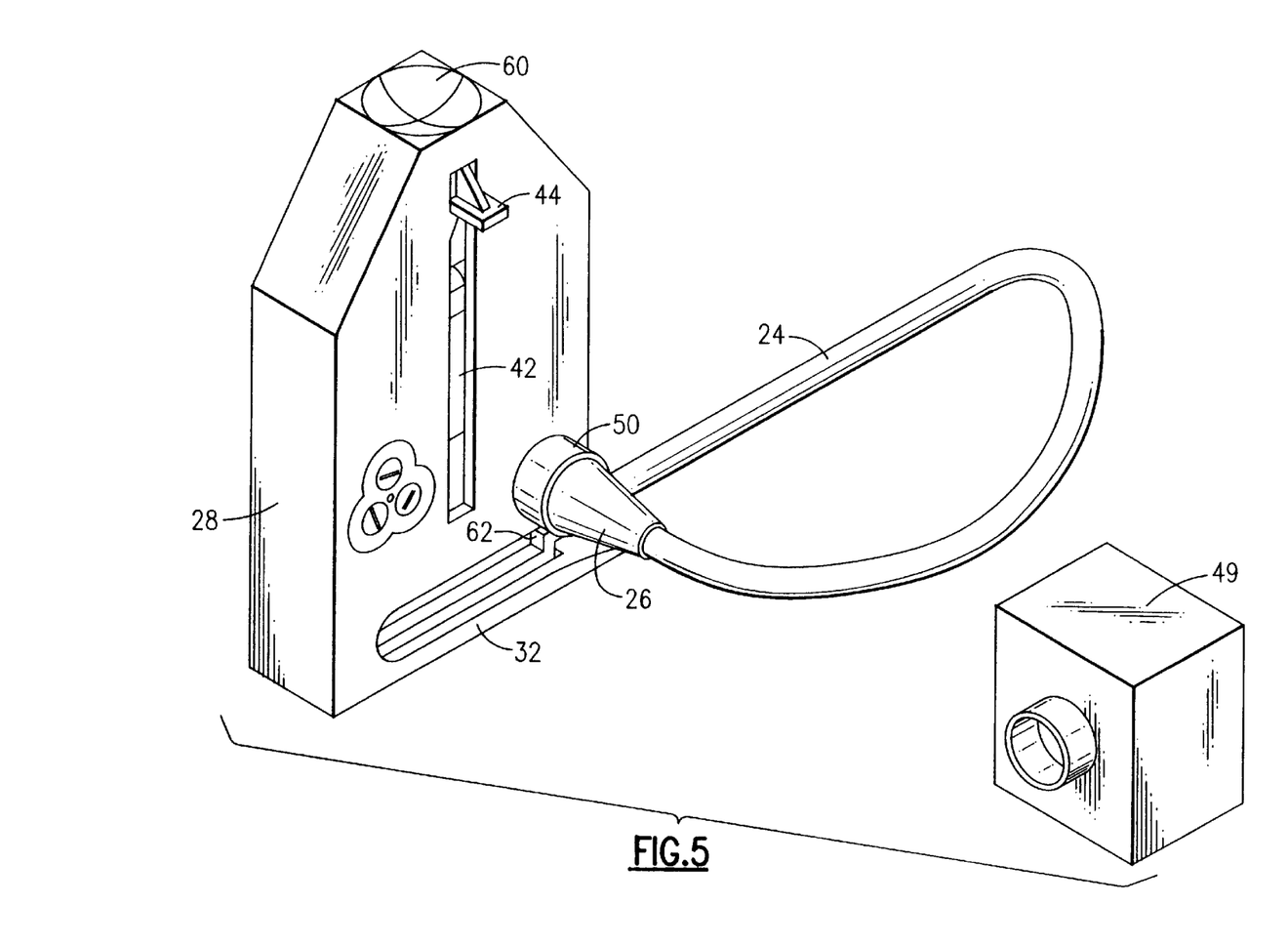
FIG. 5 illustrates a diagrammatic perspective view of the device, according to the present invention, in the second locked position with the Huber angled needle contained therein.

A Huber angled needle 16, is shown with the bent needle shaft 18 penetrating the surface of the skin 12, the subcutaneous muscle 10, and the elastomeric septum 6 into a chamber 19 of the implanted vascular port 2. The Huber angled needle 16 comprises the elongate bent needle shaft 18, a coupling hub 20, a pair of opposed handling/securing wings 22, an extension tube 24, and a female luer connector 26 (FIG. 5), which is not shown in this Figure.

With reference to FIGS. 2A through 4C, a detailed description of the present invention will now be provided. The device 27 of the present invention comprises a wall defining an exterior housing 28. The exterior housing 28, in turn, defines an interior compartment 30 therein. The exterior housing 28 is provided with a pair of spaced apart fixed legs 32 (FIG. 2C), at a lower first end thereof, and is closed at the opposite second top end thereof. The spaced apart fixed legs 32 are separated from a remainder of the exterior housing 28 by a mouth 31. Further, the pair of spaced apart fixed legs 32 are separated from one another by an elongate fixed leg slot 33 having a width greater than the diameter of the Huber needle 16 to be received therein. The purpose of the slot will be explained in further detail below.

Figure 2A:
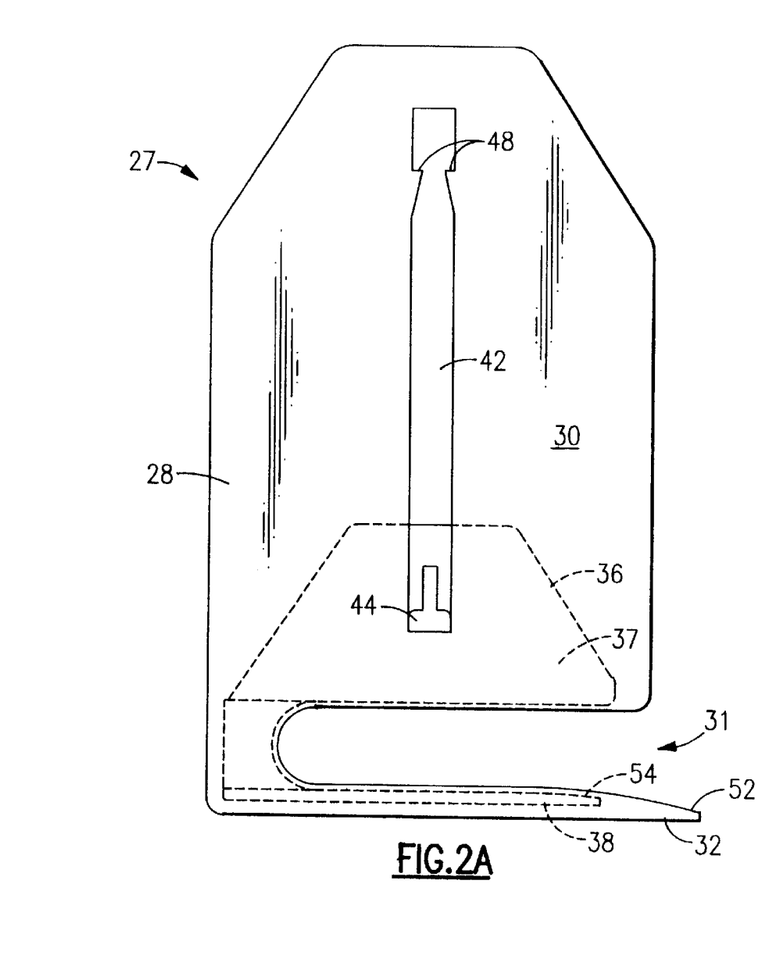
FIG. 2A illustrates a diagrammatic front elevational view of the device, according to the present invention, in an initial position with the slidable inner member shown in dashed lines.
Figure 2B:
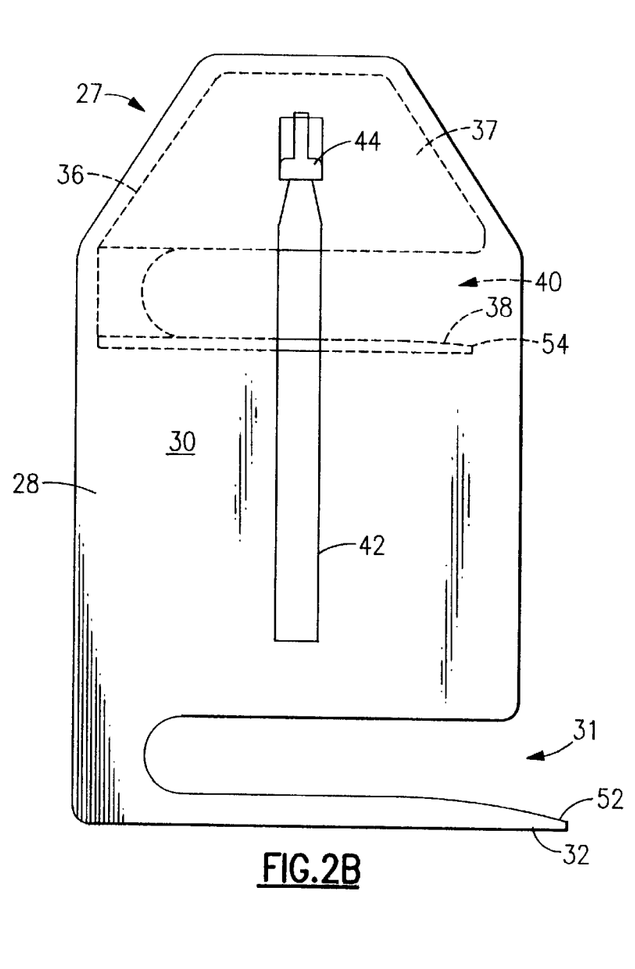
FIG. 2B illustrates a diagrammatic front elevational view of the device, according to the present invention, in a second locked position with the slidable inner member shown in dashed lines.
Figure 2C:
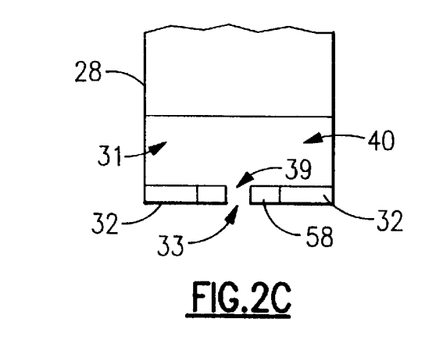
FIG. 2C is a partial diagrammatic side elevational view of the device according to the present invention.

An inner slidable member 36 is located within the interior compartment 30 of the exterior housing 28. The inner slidable member 36 comprises a main body portion 37 supporting a pair of spaced apart legs 38 which are separated from one another by an elongate movable leg slot 39 having a width slightly greater than the diameter of the Huber needle 16 to facilitate passage of the Huber needle 16 therebetween. The purpose of the elongate movable leg slot 39 will be explained in further detail below. In addition, the pair of spaced apart legs 38 are separated from the main body portion 37 of the inner slidable member 36 to define a needle removing cavity, area or surface 40 having a height greater than the diameter of the Huber needle 16 and the coupling hub 20 to facilitate receiving of the same therein. The purpose of the needle removing surface 40 surface will be explained in further detail below.

A pair of opposed side walls of the exterior housing 28 support a pair of opposed guide tracks or slots 42 which engage guide pins or tabs 44, or some other conventional guide member, supported by the inner slidable member 36 to guide and prevent tilting of the inner slidable member 36 as it moves within the interior compartment 30 of the exterior housing 28, and the purpose of such movement will be explained in further detail below. The locking tabs 44 extend through the guide slots 42 provided in the exterior housing 28 and are freely movable therealong. The end portions of the guide slots 42, located adjacent the closed end of the exterior housing 28, are each provided with a pair of inwardly facing locking protrusions 48 which allow passage of the locking tabs 44 therethrough, in one direction, but prevent passage of the locking tabs 44, in the opposite direction, to thereby permanently retain the locking tabs 44 adjacent the closed end of the exterior housing 28 once engaged therewith. By this arrangement, the locking tabs 44 permanently retain the inner slidable member 36 in a second position.

In FIG. 2A, the inner slidable member 36 is shown in the first position with the spaced apart legs 38 located outside of the interior compartment 30 of the housing 28, e.g. adjacent the mouth, for engagement with the Huber needle and for retracting the needle. Such retraction is achieve by moving the inner slidable member 36 from the first position (FIG. 2A) to the second retracted position (FIG. 2B) where the Huber needle 16 is completely retracted inside the exterior housing 28 of the device 27 to prevent an inadvertent needle stick.

Figures 4A, 4B:
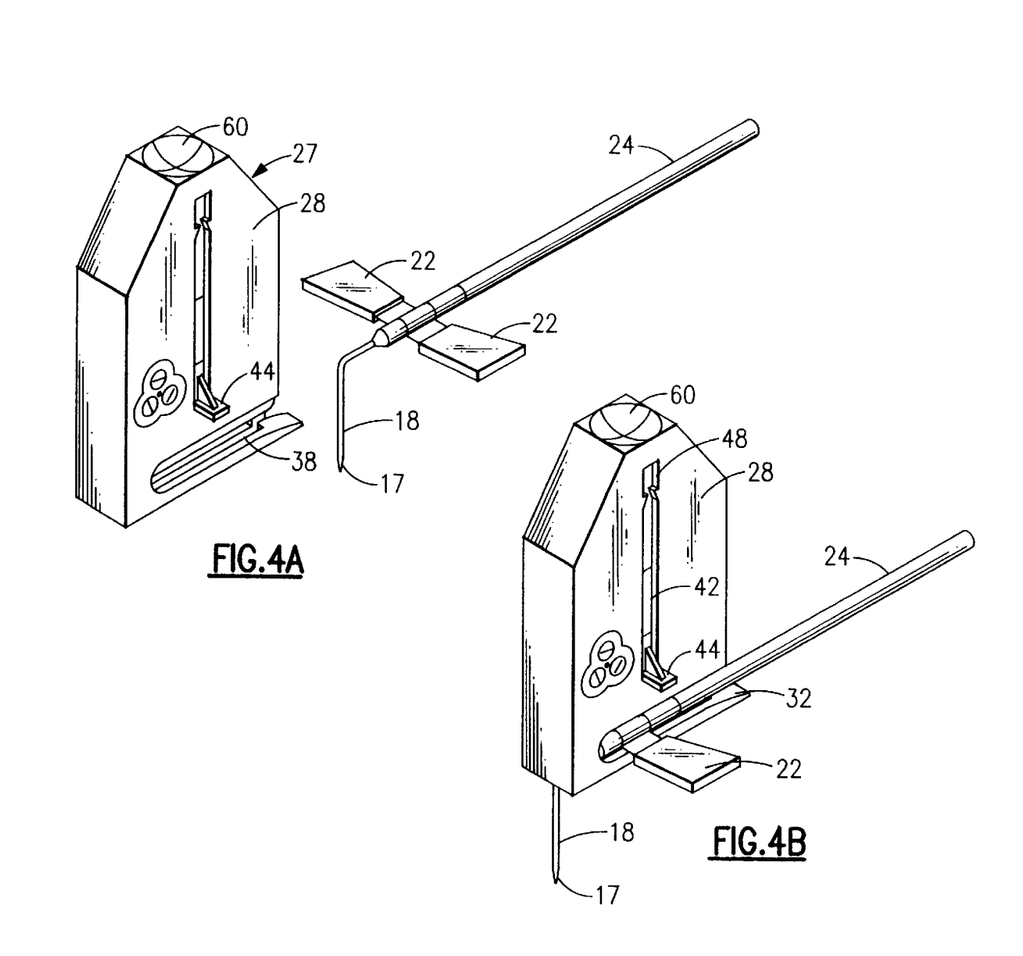
FIG. 4A illustrates a diagrammatic perspective view of the device, according to the present invention, shown separately from a Huber angled needle.
FIG. 4B illustrates a diagrammatic perspective view of the device, according to the present invention, showing its initial engaged position with the Huber angled needle.
Figure 4C:
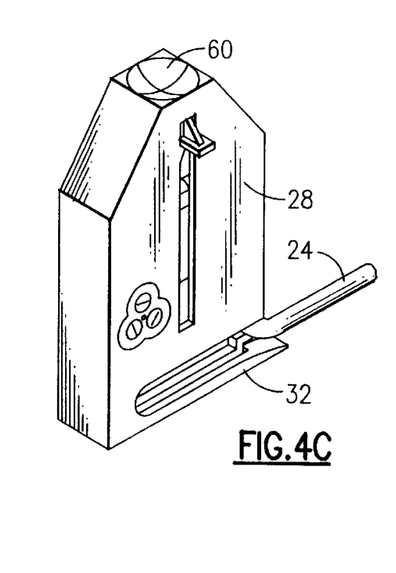
FIG. 4C illustrates a diagrammatic perspective view of the device, according to the present invention, in the second locked position with the Huber angled needle securely supported and contained therein.

With reference to FIGS. 4A–4C, use of the present invention will now be described. As can be seen in FIG. 4A, the pair spaced apart movable legs 38 are located adjacent the mouth of the device 27. With the spaced apart movable legs 38 in this position, the bent portion of the needle 18 can be readily received by the elongate fixed leg slot 33 and the elongate movable leg slot 39 (FIG. 2C) formed between the pair of spaced apart fixed and movable legs 32, 38. As the device 27 is brought into engagement with the needle/assembly (FIG. 4B), the needle is initially received by the entrance of the elongate slot 39. To facilitate engagement therewith, the leading edge of the elongate fixed leg slot 33 of the fixed legs 32 is preferably provided with a V-shaped or chamfered entrance 58 (FIG. 2C), e.g. the entrance is wider than a remainder of the elongate slot 39.

Further relative movement between the device 27 and the needle/assembly, with the pair of spaced apart fixed legs 32 and the movable legs 38 being located between an undersurface of the needle and a top surface of the skin of the patient can occur until an end surface of the needle 16 abuts against or is located closely adjacent an end surface of the inner slidable member 36. Once such engagement occurs, safe retraction of the needle 16 can then occur. This is achieved by the care giver grasping the opposed locking tabs 44 and moving them from the position shown in FIG. 4B to the position shown in FIG. 4C whereby the locking tabs 44 are moved along the guide slot 42 past the locking protrusions 48 so as to permanently retain the inner slidable member 36 in the second position. During movement of the locking tabs 44 along the housing slot 42, the inner slidable member 36 is guided along the guide slots 42 via the associated guide locking tabs 44.

Figure 3:
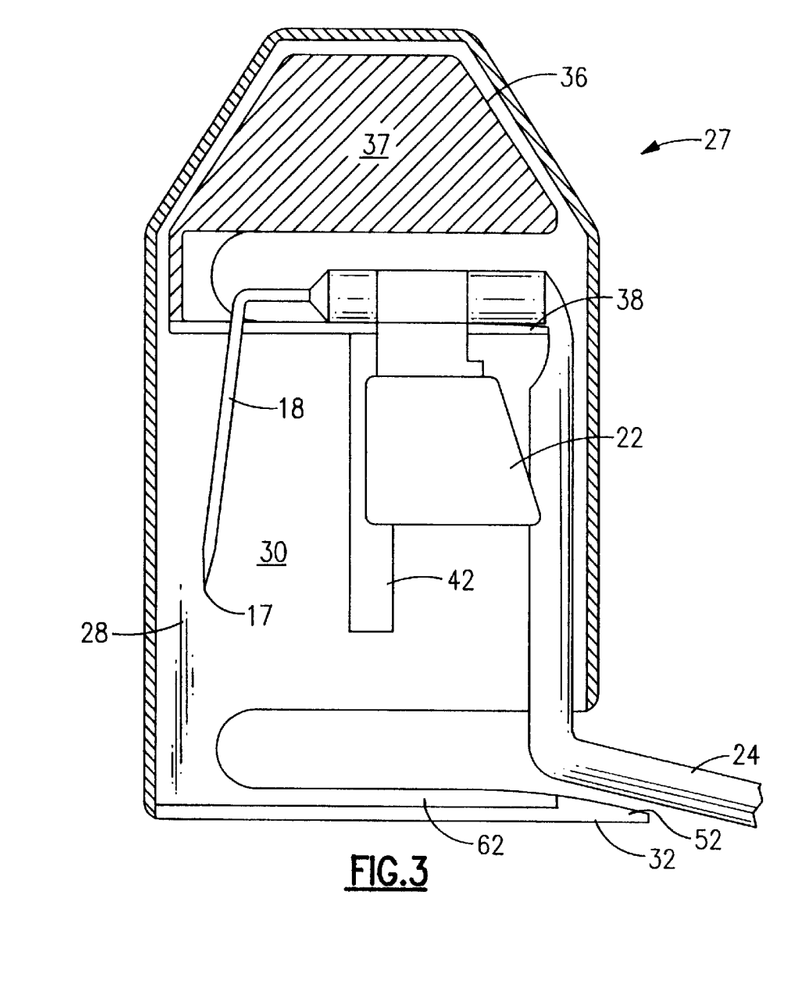
FIG. 3 illustrates a diagrammatic cross-sectional view of the device, according to the present invention, in the second locked position supporting and encasing a Huber needle in dashed lines.

The completely retracted position of the needle 16 can be seen in FIGS. 3 and 4C. Once the needle is completely retracted, the engagement between the locking tabs 44 and the locking protrusion 48 prevent movement of the inner slidable member 36 from the second position and maintains the needle completely within the exterior housing 28 whereby the needle can not stick another person. Thereafter, the female luer connector 26, attached to opposite end of the extension tube 24, can be disconnected from a desired supplied device 49 (FIG. 5) and connected to a male luer connector 50 supported by an outer surface of the exterior housing 28. This arrangement allows the removed male or female luer connector to be coupled to the exterior housing 28 to render the device slightly more compact for disposal purposes.

It is to be appreciated that the components of the device can be manufactured from plastic, metal or any other suitable material. Preferably at least one of the spaced apart movable legs 38 and/or the fixed legs 32 is tapered 52, 54, at a free end thereof, to facilitate locating the device 27 between an undersurface of the needle 16 and a surface of the skin 12. Preferably the leading edge of at least the fixed leg slot 33 is provided with a V-shaped or chamfered entrance 58 (FIG. 2C) and possibly the leading edge of the elongate movable leg slot 39 may also be provided with a V-shaped or chamfered entrance to facilitate receipt of the needle 16 between by the pair of legs. Lastly, a concave depression or section 60 can be provided in the top surface of the device 27 to facilitate the engagement of the device 27 by the hand of the user, e.g. typically the care giver will place his/her thumb on the concave section 60 and will locate his/her index and middle fingers of the same hand on the undersurface of the two opposed locking tabs 44. The index and middle fingers are then moved in a direction towards the thumb which moves the locking tabs 44 and, in turn, the inner slidable member 36 from its first to its second locked position whereby the Huber needle 16 is removed from the vascular port 2 and safely and completely retracted inside the device 27. Following the retraction of the Huber needle 16 into the device 27 and locking of the inner slidable member 16 in its second position, the entire device 27 including the Huber needle 16 can be disposed of into a biohazard sharps container.

It is to be appreciated that each of the fixed legs of the exterior housing 28 are provided with a recessed area 62 (FIG. 5) to facilitate receiving the movable legs 38 of the inner slidable member 36, which are typically shorter in length than the fixed legs 32. Further, movement of the inner slidable member 36 must be of sufficient distance to insure that the pointed tip 17 of the needle 16 is completely retracted inside the interior compartment 30 to prevent an inadvertent needle stick.

An important aspect of the present invention is that the slidable member have a needle receiving area, surface recess, or cavity for receiving, supporting, engaging or grasping a portion of the needle to be removed to facilitate removal of the needle from a patient. Further, said slidable member must be movable from a first position in which a least a portion of said needle receiving area, surface recess, or cavity is located adjacent said mouth of said needle retraction device, for receiving the needle, to a second retracted position in which said needle receiving surface, along with a supported needle, are completely retracted inside said interior compartment of said exterior housing to prevent an inadvertent stick of the needle. As there are a variety of other possible arrangement for the slidable member which would be readily apparent to one skill in the art, a further detailed description concerning the same is not provided herein.

It is also to be appreciated that a variety of different known locking mechanisms can be utilized to lock the inner slidable member in the second position. As such other locking arrangements are well known to those skilled in this art, a further detailed description concerning the same is not provided herein.

Since certain changes may be made in the above described device and method, without departing from the spirit and scope of the invention herein involved, it is intended that all of the subject matter of the above description or shown in the accompanying drawings shall be interpreted merely as examples illustrating the inventive concept herein and shall not be construed as limiting the invention.

It is claimed:

1. A needle retraction device for removing a needle from a patient, said needle retraction device comprising:
    an exterior housing defining an interior compartment and a mouth;
    a slidable member having a needle receiving surface for receiving a needle therein to assist with removal of the needle from a patient; and
    said slidable member being movable from a first position in which at least a portion of said needle receiving surface is located adjacent said mouth of said needle retraction device, for receiving the needle, and a second retracted position in which said needle receiving surface, along with a supported needle, are completely retracted inside said interior compartment of said exterior housing to prevent an inadvertent stick of the needle.

2. A needle retraction device according to claim 1, wherein said needle receiving surface is defined by a pair of movable legs separated from one another by an elongate slot, and said pair of movable legs are spaced from a remainder said slidable member by an area which is sized to receive a needle therein.

3. A needle retraction device according to claim 1, wherein said needle retraction device includes a locking mechanism to lock said slidable member in said second position.

4. A needle retraction device according to claim 2, wherein said exterior housing includes a pair of fixed legs which are spaced apart from one another by an longate housing slot and said pair of movable legs are located adjacent to said pair of fixed legs.

5. A needle retraction device according to claim 1, wherein an exterior wall of said housing is provided with at least one elongate guide slot and said inner slide member is provided with at least one locking tab, and said at least one said locking tab is movable along said at least one elongate guide slot from said first position to said second position.

6. A needle retraction device according to claim 5, wherein at least one locking protrusion is provided in said at least one elongate guide slot for engaging and permanently retaining said at least one locking tab when engaged therewith.

7. A needle retraction device according to claim 4, wherein at least one of said pair of movable legs and said pair of fixed legs is provided with a chamfered entrance to facilitate receiving said needle therein.

8. A needle retraction device according to claim 4, wherein at least one of said pair of movable legs and said pair of fixed legs is provided with a taper surface to facilitate locating said device between said needle and skin of a patient.

9. A needle retraction device according to claim 1, wherein an inner surface of said exterior housing supports a pair of opposed guide tracks which each engage an associated guide member, carried by said slidable member, for guiding said slidable member during movement within said interior compartment.

10. A needle retraction device according to claim 1, wherein a concave section is provided in a surface of said device, remote from said mouth, to facilitate engagement of said device by a hand of a user.

11. A needle retraction device according to claim 2, used in combination with a Huber angled needle, said Huber angled needle being connected to an extension tube for supplying a desired fluid to be dispensed to a patient, and said Huber angled needle further including a pair of wings to facilitate use and securement of said Huber angled needle.

12. The combination according to claim 11, wherein said elongate slot of said pair of movable legs is wide enough to allow said Huber angled needle to pass therethrough, but narrower than said extension tube so as to facilitate retraction of said Huber angled needle inside said interior compartment of said exterior housing.

13. The combination according to claim 11, wherein a remote end of said extension tube is provided with a luer connector for facilitating connection of said extension tube of said Huber angled needle to a desired dispensing device.

14. A needle retraction means for removing a needle from a patient, said needle retraction means comprising:
    housing means defining an interior compartment and mouth means;
    slidable means having needle receiving means for receiving a needle therein to assist with removal of the needle from a patient; and
    said slidable means being movable from a first position in which at least a portion of said needle receiving means is located adjacent said mouth means of said needle retraction means, for receiving the needle, and a second retracted position in which said needle receiving means, along with a supported needle, are completely retracted inside said interior compartment of said housing means to prevent an inadvertent stick of the needle.

15. A needle retraction means according to claim 14, wherein said needle receiving means is defined by a pair of movable legs separated from one another by an elongate slot, and said pair of movable legs are spaced from a remainder said slidable means by an area which is sized to receive a needle therein.

16. A needle retraction means according to claim 14, wherein said needle retraction means includes locking means to lock said slidable means in said second position.

17. A needle retraction means according to claim 14, wherein said housing means includes a pair of fixed legs which are spaced apart from one another by an elongate housing slot and said pair of movable legs are located adjacent to said pair of fixed legs.

18. A needle retraction means according to claim 14, wherein an exterior wall of said housing is provided with at least one elongate guide slot and said slide means is provided with locking means, and said locking means is movable along said at least one elongate guide slot from the first position to the second position.

19. A method of removing a Huber angled needle from a patient with a needle retraction device, said method comprising the steps of:

defining an interior compartment by an exterior housing;

at least partially accommodating, within said exterior housing, a slidable member having a needle receiving surface for receiving a needle therein to assist with removal of the needle from a patient;

receiving the needle by said slidable member when said slidable member is in a first position in which at least a portion of said needle receiving surface is located adjacent said mouth of said needle retraction device; and moving said slidable member, along with a supported needle, to a second retracted position in which said slidable member is completely retracted inside said interior compartment of said exterior housing to prevent an inadvertent stick of the needle.

20. The method according to claim 19, further comprising the steps defining said needle receiving surface by a pair of movable legs separated from one another by an elongate slot, and spacing said pair of movable legs from a remainder said slidable member by an area which is sized to receive a needle therein.

21. A needle retraction device for removing a needle from a patient, said needle retraction device comprising:

an exterior housing defining an interior compartment and a mouth;

a movable member having a needle receiving surface for receiving a needle therein to assist with removal of the needle from a patient; and said movable member being movable from a first position in which at least a portion of said needle receiving surface is located adjacent said mouth of said needle retraction device, for receiving the needle, and a second retracted position in which said needle receiving surface, along with a supported needle, are completely retracted inside said interior compartment of said exterior housing to prevent an inadvertent stick of the needle.

* * * * *